(12) United States Patent
Liu

(10) Patent No.: US 8,878,145 B1
(45) Date of Patent: Nov. 4, 2014

(54) APPARATUS AND METHOD FOR FLUORESCENCE SPECTRAL AND COLOR MEASUREMENTS OF DIAMONDS, GEMSTONES AND THE LIKE

(76) Inventor: Yan Liu, Monterey Park, CA (US)

( * ) Notice: Subject to any disclaimer, the term of this patent is extended or adjusted under 35 U.S.C. 154(b) by 0 days.

(21) Appl. No.: 13/560,202

(22) Filed: Jul. 27, 2012

(51) Int. Cl.
*G01N 21/64* (2006.01)
*F21K 2/00* (2006.01)

(52) U.S. Cl.
USPC ........................................ 250/461.1

(58) Field of Classification Search
USPC ........................................ 250/461.1
See application file for complete search history.

(56) References Cited

U.S. PATENT DOCUMENTS

| | | | |
|---|---|---|---|
| 3,936,190 | A | 2/1976 | Ohnishi et al. |
| 4,022,529 | A | 5/1977 | White |
| 5,721,613 | A | 2/1998 | Linowski et al. |
| 5,801,819 | A | 9/1998 | Spear et al. |
| 5,888,846 | A * | 3/1999 | Miyata et al. ............... 438/105 |
| 7,102,742 | B2 | 9/2006 | Geurts |
| 7,262,835 | B2 | 8/2007 | Geurts |
| 7,652,755 | B2 | 1/2010 | Liu |
| 2010/0044589 | A1 * | 2/2010 | Garcia et al. ............... 250/492.1 |
| 2011/0260079 | A1 * | 10/2011 | Tokhtuev et al. ......... 250/461.1 |

FOREIGN PATENT DOCUMENTS

| | | | |
|---|---|---|---|
| EP | 0425426 A2 | * | 5/1991 |
| EP | 425426 A2 | * | 5/1991 |
| WO | WO 2008124542 A1 | * | 10/2008 |

* cited by examiner

*Primary Examiner* — David Porta
*Assistant Examiner* — Abra Fein
(74) *Attorney, Agent, or Firm* — Thomas I. Rozsa

(57) ABSTRACT

An apparatus and method for fluorescence spectral and color measurements of diamonds, gemstones and the like. The apparatus comprises a spectrometer, and computer and a dual integrating sphere measurement arrangement comprising a measurement integrating sphere, a sample integrating sphere, a sample platform, a lens system, a baffle, an ultraviolet radiation source on the top of the sample integrating sphere, and another light source attached to the measurement integrating sphere. The sample on the sample platform is radiated by the ultraviolet radiation source on the top of the measurement integrating sphere. The sample emits fluorescent light into the measurement integrating sphere, and the fluorescent light is received by the lens system. The spectrometer separates the fluorescent light into spectral signals, and the computer calculates the fluorescence spectrum and colorimetric data.

17 Claims, 2 Drawing Sheets

APPARATUS AND METHOD FOR FLUORESCENCE SPECTRAL AND COLOR MEASUREMENTS OF DIAMONDS, GEMSTONES AND THE LIKE

BACKGROUND OF THE INVENTION

1. Field of the Invention

The present invention relates to an apparatus and method for ultraviolet fluorescence spectral and color measurements of diamonds, gemstones and the like, and more particularly, to an apparatus and method for measuring the ultraviolet fluorescence spectrum and for calculating the colorimetric data of the ultraviolet fluorescence caused by the ultraviolet radiation of an ultraviolet radiation source in the wavelength range from 200 nm through 400 nm.

2. Description of the Prior Art

Fluorescence is usually measured by fluorescence spectrometers. A fluorescence spectrometer consists of two monochromators. One monochromator provides excitation radiation on a fluorescence sample wavelength by wavelength in the ultraviolet wavelength range, and another monochromator separates the fluorescence emission from the sample into a spectrum in the visible wavelength range for fluorescence spectral measurement (Ohnishi et al, U.S. Pat. No. 3,936,190; White, U.S. Pat. No. 4,022,529; and Linowski et al, U.S. Pat. No. 5,721,613). At each ultraviolet radiation wavelength from the excitation monochromator, the measurement monochromator scans the fluorescence emission in the whole measurement wavelength range. The total emission power of the fluorescence is the sum of the fluorescence emissions measured in the whole measurement wavelength range by the measurement monochromator wavelength by wavelength of the ultraviolet excitation radiation.

Spear et al (U.S. Pat. No. 5,801,819) discloses an apparatus for distinguishing a natural, colorless, or near colorless diamond from a synthetic diamond. The apparatus has a chamber with a flash lamp to provide ultraviolet light below 250 nm. The intensity of ultraviolet fluorescence of a diamond is measured to classify the diamond as probably natural or synthetic.

The intensity and color of fluorescence of diamonds and gemstones are traditionally observed and graded visually by human graders. Under an ultraviolet fluorescent lamp at 365 nm, a human grader observes the color and intensity of the ultraviolet fluorescence of a diamond, and compares the fluorescence intensity of the diamond with the fluorescence intensities of a fluorescence grading master set to assign a fluorescence grade to the diamond graded.

The fluorescence of diamonds and gemstones can also be graded by a diamond fluorescence measuring device (Geurts, U.S. Pat. No. 7,102,742 and U.S. Pat. No. 7,262,835). The device includes a sample chamber with two ultraviolet light emitting diodes (LED) and a light detector. The measured lux reading of the visible fluorescence light is converted into fluorescence grades.

Liu (U.S. Pat. No. 7,652,755) discloses an apparatus and method for color measurement and color grading of diamonds, gemstones and the like. The apparatus comprises a spectrometer, a computer and a dual integrating sphere measurement arrangement. The dual integrating sphere optical arrangement consists of two integrating spheres. One is a measurement integrating sphere and another is a sample integrating sphere. The apparatus can measure the spectral reflectance of a faceted diamond, gemstone or the like in the visible wavelength range, calculate the colorimetric data, and grade the color using the artificial intelligence software with a neural network and a fuzz logic algorithm.

There is no apparatus in the prior art capable for directly measuring ultraviolet fluorescence spectrum and fluorescence color of gemstones, diamonds and the like. There is a need for such an apparatus capable for directly measuring the ultraviolet fluorescence spectrum and fluorescence color diamonds, gemstones, and the like.

SUMMARY OF THE INVENTION

One object of the present invention is to provide an ultraviolet fluorescence spectral measurement apparatus and method that can accurately measure the ultraviolet fluorescence spectrum and fluorescence color of diamonds, gemstones and the like.

A second object of the invention is to provide an ultraviolet fluorescence spectral measurement apparatus that is practical for use, readily inexpensive to manufacture and commercially available to consumers.

A third object of the invention is to provide the ultraviolet fluorescence measurement apparatus with a method to measure the ultraviolet fluorescence color of diamonds, gemstones and the like.

A fourth object of the invention is to provide the ultraviolet fluorescence measurement apparatus with a method to calculate the colorimetric data of the ultraviolet fluorescence color of diamonds, gemstones and the like.

To achieve these and other advantages and in accordance with the purpose of the invention, as embodied and broadly described herein, the invention provides an apparatus and method for measuring the ultraviolet fluorescence spectrum and color of gemstones, diamonds and like. The method includes steps of inputting physical parameters, calculating the measurement parameters, selecting ultraviolet radiation source and wavelength of ultraviolet radiation, measuring the ultraviolet fluorescence spectrum, and calculating colorimetric data from the ultraviolet fluorescence spectrum.

To implement the method, the apparatus should include a spectrometer, a computer, a dual integrating sphere measurement arrangement comprising a sample integrating sphere with an ultraviolet radiation source, a measurement integrating sphere, a measurement platform, a measurement aperture, a measurement aperture filter, a lens system, a light trap and a baffle. The ultraviolet radiation source radiates a sample on the middle of the platform from the top of the sample integrating sphere. The lens system in the measurement integrating sphere receives the ultraviolet fluorescent light from the sample, focuses the fluorescent light into a fiber optic cable, and sends the fluorescent light to the spectrometer through the fiber optic cable. The spectrometer separates the ultraviolet fluorescent light into fluorescence spectral signals. Then, the computer calculates the fluorescence spectrum and the chromatic data. The apparatus can measure the ultraviolet fluorescence spectrum and color of faceted and rough diamonds, gemstones, and the like in any shape, size, refraction index, and weight.

The invention can be summarized as follows:

A fluorescence spectral measurement and fluorescence color measurement apparatus comprising: a measuring means for measuring the fluorescence spectrum of a sample:

a dual integrating sphere measurement arrangement that is configured to house a sample, provide ultraviolet radiation on the sample, collect fluorescent light from the sample, and transmit the fluorescent light to the measuring means; a means that is configured to separate the fluorescent light into a spectrum, convert the spectrum into digital signals, and send the digital signals to the calculation means; a computer that is configured to calculate the measurement parameters, control the measuring means; calculate the fluorescence spectrum; and calculate the fluorescence color; said dual integrating sphere measurement arrangement is comprised of: a sample integrating sphere that is configured to provide a diffuse white measuring environment for a sample, which sample integrating sphere has a bottom, an internal area, an ultraviolet emission source, and an open area;

a measurement integrating sphere with at least one lens system port, a light port, and internal area, an open area, and a top; a sample platform connecting the measurement integrating sphere to the sample integrating sphere, which sample platform has a an upper surface, a bottom surface, and a middle, and which platform contains a round hole called a measurement aperture; a measurement aperture filter set on the platform, which measurement aperture filter is configured to accommodate a sample; a lens system attached to the measurement integrating sphere and configured to receive fluorescent light from the sample; an ultraviolet emission source that is configured on the top of the sample integrating sphere to provide ultraviolet radiation.

The present invention is also a dual integrating sphere measurement arrangement wherein the bottom of said sample integrating sphere which is on the upper surface of said platform is on the top of said measurement integrating sphere.

The present invention is also a dual integrating sphere measurement arrangement wherein the said sample integrating sphere can be taken off of the apparatus, and the sample integrating sphere can be placed back onto the apparatus.

The present invention is also a dual integrating sphere measurement arrangement wherein the open area of said sample integrating sphere is equal to or larger than said measurement aperture filter and exceeds 1 percent of the internal area of the sample integrating sphere.

The present invention is also a dual integrating sphere measurement arrangement wherein the total area of the measurement aperture, light trap, lens system port and light port of said measurement integrating sphere does not exceed 50 percent of the internal area of the measurement integrating sphere.

The present invention is also a dual integrating sphere measurement arrangement wherein said measurement aperture filter is set in the middle of said sample platform.

The present invention is also a dual integrating sphere measurement arrangement wherein said measurement aperture filter comprises one or more layers of materials capable of transmitting ultraviolet light and visible light in the wavelength range from 200 nm through 800 nm.

The present invention is also a dual integrating sphere measurement arrangement wherein the view field of said lens system is restricted to said measurement aperture with a 1 to 25 degree viewing angle from normal to said measurement aperture.

The present invention is also a dual integrating sphere measurement arrangement wherein said sample integrating sphere is configured to accommodate the sample in the middle of said measurement aperture filter in a table-down position.

The present invention is also a dual integrating sphere measurement arrangement means selected from the group consisting of a spectrometer, spectrophotometer, spectral imaging system, spectral graphic system and spectroradiometer.

The present invention is also a dual integrating sphere measurement arrangement wherein said ultraviolet emission source is installed on the top of the sample integrating sphere to provide ultraviolet radiation on the sample.

The present invention is also an ultraviolet emission source which is selected from the group consisting of an ultraviolet lamp, an ultraviolet fluorescence lamp, an arc lamp, a filtered arc lamp, an ultraviolet laser, and a light emitting diode (LED).

The present invention is also an ultraviolet emission source wherein the ultraviolet emission source emits ultraviolet radiation in the wavelength range from 200 nm to 400 nm.

The present invention is also an ultraviolet emission source wherein the ultraviolet emission source emits short wavelength ultraviolet radiation at 254 nm of mercury emission line for short wavelength ultraviolet fluorescence measurement.

The present invention is also an ultraviolet emission sources wherein said ultraviolet emission source emits long wavelength ultraviolet radiation at 365 nm of mercury emission line for long wavelength ultraviolet fluorescence measurement.

The present invention is also an ultraviolet emission sources wherein said ultraviolet emission source is powered by a group of electric power supplies selected from the group consisting of switch power supply, regular power supply, and specially designed power supplies.

The present invention is also an ultraviolet emission sources wherein said ultraviolet emission source is directly powered by a 5 volt, direct current power supply provided by the Universal Serial Bus (USB) of a computer or other devices through the USB port.

The present invention is also an ultraviolet emission sources wherein said ultraviolet emission source is connected to a group of electronic circuits selected from the group consisting of a current limiting resistor in series, a voltage converter, a voltage regulator, a current regulator, and a voltage divider.

The group of electronic circuits wherein said group of electronic circuits are powered by a group of electric power supplies are selected from the group consisting of a switch power supply, a regular power supply, and specially designed power supplies.

The present invention is also a group of electronic circuits wherein said group of electronic circuits are powered by the 5 volt, direct current power supply provided by the USB of a computer or other devices through the USB port.

The present invention is also a measuring means wherein said measuring means is controlled by said measurement parameters calculated by said mathematics methods.

the present invention also includes measurement parameters wherein the measurement parameters can be adjusted manually.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
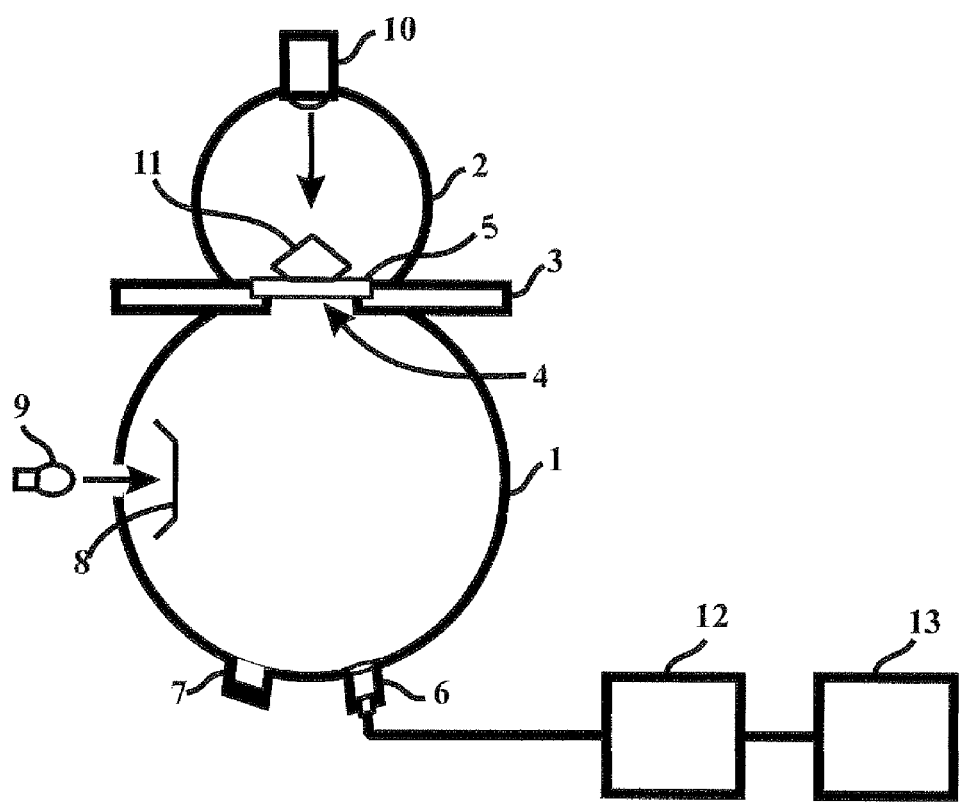
FIG. 1 is a schematic depicting an apparatus of the present invention with a computer, a spectrometer and the dual integrating sphere measurement arrangement including (1) Measurement integrating sphere; (2) Sample integrating sphere; (3) Sample platform; (4) Measurement aperture; (5) Measurement aperture filter; (6) Lens system; (7) Light trap; (8) Baffle; (9) light source: (10) Ultraviolet radiation source; (11) Sample: (12) Spectrometer; and (13) Computer.

FIG. 1 shows an apparatus according to an embodiment of the present invention for ultraviolet fluorescence spectral measurement and fluorescence color measurement of diamonds, gemstones and the like. The apparatus includes a spectrometer 12, a computer 13, and the measurement arrangement including a measurement integrating sphere 1, a sample integrating sphere 2, a sample platform 3, a measurement aperture 4, a measurement aperture filter 5, a lens system 6, a light trap 7, a baffle 8, a light source 9, and an ultraviolet radiation source 10.

The measurement integrating sphere 1 and the sample integrating sphere 2 are connected together by the sample platform 3. In the middle of the platform 3 there is a round hole called measurement aperture 4. The measurement aperture filter 5 is set in the middle of the platform 3, and the measurement aperture is in the middle of the measurement aperture filter. The sample 11, usually a faceted diamond, a faceted gemstone or the like, is placed table-down on the measurement aperture filter 5 inside the sample integrating sphere 2.

The sample integrating sphere 2 is on the top of the measurement integrating sphere 1 as illustrated in FIG. 1. The inside walls of the measurement integrating sphere 1 and the sample integrating sphere 2 are coated with a high reflectance material, such as barium sulphate ($Ba_2SO_4$) or polytetrafluoroethylene (PTFE).

The sample integrating sphere 2 can be opened for accommodating the sample on the center of the measurement aperture filter 5 for measurement. The sample is placed at the table-down position in the center of the measurement aperture filter 4. The sample is actually held by the gravity; therefore no sample holder accessory is necessary. The total area of the measurement aperture 4, the output port of the lens system 6, the light trap 7 and the light port for the light source 9 shall be less than 10% of the total internal sphere area of the measurement integrating sphere 1. The open area of the sample integrating sphere 2 is equal to or larger than that of the measurement aperture filter 4. The measurement integrating sphere 1 is attached with the lens system 6, the light trap 7, the baffle 8, and the light source 9.

The main function of the measurement integrating sphere is to collect the ultraviolet fluorescent light from the sample 11, and to transmit the collected fluorescent light from the sample 11 to the spectrometer 12 by the lens system 6 through a fiber optic cable.

The visible light source 9 is not used for the ultraviolet fluorescence spectral measurement and fluorescence color measurement described herein.

According to another aspect of the invention, the ultraviolet radiation source 10 on the top of the sample integration sphere 2 radiates ultraviolet radiation on the sample 11 on the measurement aperture filter 5. The sample 11 emits ultraviolet fluorescent light into the measurement integration sphere 1. The spectrometer 12 receives fluorescent light collected by the lens system 6, separates the fluorescent light into a spectrum, and converts the spectral intensities into digital accounts for the computer 13 to calculate the fluorescence spectrum and the colorimetric data.

According to another aspect of the invention, the wavelength of the ultraviolet emission source 10 on the top of the sample integration sphere 2 can be changed in the wavelength range from 200 nm in the short ultraviolet wavelength through 400 nm in the long ultraviolet wavelength. For the particular applications of ultraviolet fluorescence measurement of diamonds, gemstones and the like, the ultraviolet radiation source of a mercury lamp at 254 nm is used as the short wavelength ultraviolet radiation source, and the ultraviolet radiation lamp of mercury at 365 nm is used as the long ultraviolet wavelength radiation source.

The measurement aperture filter 5 transmits ultraviolet and visible light in the wavelength range from 200 nm through 1000 nm. The short cut wavelength of the filter is longer that the wavelength of the ultraviolet radiation source, and is shorter or equal to the shortest wavelength of the fluorescence measurement. For a particular wavelength range of fluorescence measurement of diamonds, gemstones and like from 380 to 760 nm, the short cut wavelength of the filter is at 365 to 380 nm when the long wavelength ultraviolet radiation source of 365 nm is used, and at 265 to 380 nm when the short wavelength ultraviolet radiation source of 254 nm is used.

Figure 2:
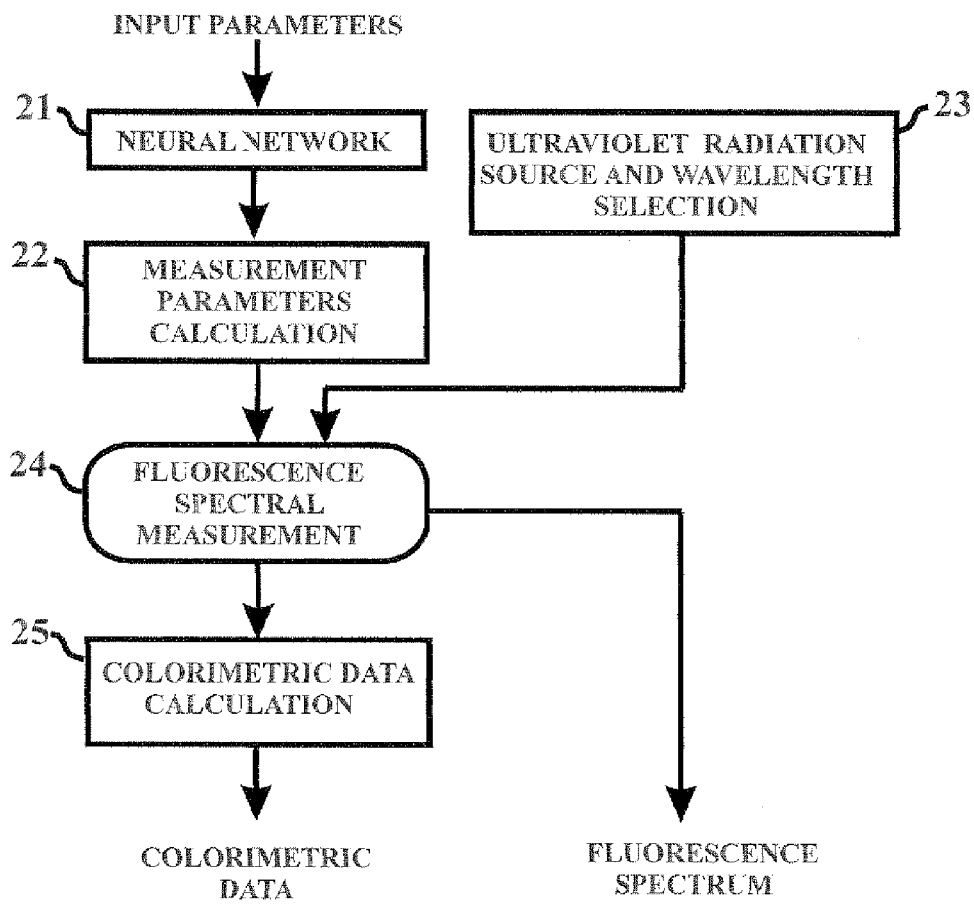
FIG. 2 is a flowchart depicting the method of fluorescence spectral measurement and fluorescence color measurement.

The lens system 6 is installed in a fiber optic port of the measurement integrating sphere 1. The view field of the lens system 6 is restricted to the measurement aperture 4 with a divergence of about 2 to 5 degree. With reference to FIG. 2, a flow diagram illustrates the methods of the present invention. The method includes the steps of input parameters into the neural network 21, measurement parameters calculation 22, selecting ultraviolet radiation source and wavelength 23, fluorescence spectral measurement and output fluorescence spectrum measured 24, and colorimetric calculation and output colorimetric data 25.

The computer 13 receives the physical parameters of the sample measured into the neural network 21, calculates the fluorescence measurement parameters 22, controls the spectrometer to measure the spectral radiation of the fluorescence 24 under the ultraviolet radiation source at the selected wavelength 23 and outputs the spectrum of the ultraviolet fluorescence, and calculates the colorimetric data 25 and output the colorimetric data of the ultraviolet fluorescence measured.

The first step of the method is to input physical parameters 21 to the computer 13. The physical parameters include, but are not limited to, a shape of the sample, three dimensions of the sample, namely length, width and depth, refractive index, and cut grade. Faceted gemstones can be in any shapes, and it is impossible to list all of the shapes for input. As an approximate approach, input parameters into the neural network step 21 of the preferred embodiment only includes the most popular shapes of round, oval, rectangle, marquise, and heart. Other shapes shall be substituted by the above-listed shapes with the most similar shapes. The princess cut, for example, can be substituted by the rectangle shape.

The three dimensions are in the unit of millimeter. The refractive index of a gemstone can be measured by a refractometer or other physics methods. The refractive index can also be obtained by checking references, such as books and articles.

In the step of measurement parameters calculation 22, the parameters for controlling the spectrometer are calculated by mathematical algorithms. The mathematic algorithms are one or more of artificial neural network, optimization, fuzzy logic and regression. The algorithm of the artificial neural network 21 is particularly advantageous to calculate the parameters for controlling the spectrometer 12. The calculated measurement parameters include, but not limited to, measurement time, number of measurement, bandwidth, the width of slit, the voltage of detector, etc.

In the step of ultraviolet radiation source and wavelength selection 23, an ultraviolet radiation source at a particular wavelength or a particular range of ultraviolet wavelengths is selected to radiate the sample 11 for the fluorescence spectral measurement and color measurement. The ultraviolet radiation source can be selected from the group consisting of an ultraviolet lamp, an ultraviolet fluorescence lamp, an arc lamp, a filtered arc lamp, an ultraviolet laser, or a light emitting diode (LED). The ultraviolet wavelength range is from 200 nm through 400 nm. For ultraviolet fluorescence measurement of diamonds, gemstones and like, the mercury ultraviolet lamp of short ultraviolet wavelength at 245 nm is usually selected for short wavelength ultraviolet fluorescence measurement, and the light emitting diode of long ultraviolet wavelength at 265 nm is preferably selected. Both the short and long ultraviolet wavelengths are the atomic excitation wavelengths of mercury.

In the step of ultraviolet radiation source and wavelength selection 23, a light emitting diode (LED) at a particular wavelength or a particular range of ultraviolet wavelength are selected to radiate the sample 11 for the fluorescence spectral measurement and color measurement. The ultraviolet wavelength range of the light emitting diode (LED) radiates ultraviolet radiation in the wavelength range from 200 nm through 400 nm. For ultraviolet fluorescence measurement of diamonds, gemstones and like, the light emitting diode (LED) of short ultraviolet wavelength at 245 nm is selected for short wavelength ultraviolet fluorescence measurement, and the light emitting diode of long ultraviolet wavelength at 265 nm is preferably selected. Both the short and long ultraviolet wavelengths are the atomic excitation wavelengths of mercury.

The working voltage of the ultraviolet light emitting diode is in the range of 3-5 volts. The output power of the universal serial bus (USB) of the computer is 5 volt. The ultraviolet light emitting diode can be provided directly by the universal serial bus (USB) of computer. If the working voltage of an ultraviolet light emitting diode is lower than 5 V, a current limiting resistor in series is used to provide correct voltage on the ultraviolet light emitting diode. The measurement parameters calculated in the step 22 are sent to the spectrometer 12 for the fluorescence spectral measurement 23. The spectrometer 12 uses the measurement parameters to set its measurement condition, and then to measure the ultraviolet fluorescence spectrum. The spectrometer 12 outputs a digital count file $S(\lambda)$ to the computer 13 to +calculate the fluorescence spectrum under the ultraviolet radiation source at the wavelength selected in step 23.

According to another aspect of the invention, the spectrometer is calibrated by a standard spectral radiation source with known spectral radiance $P_s(\lambda)$ and by a standard black tile with known spectral reflectance $R_b(\lambda)$.

The spectrum of fluorescence radiation is measured in step 24. The ultraviolet fluorescence spectrum of the sample is calculated by the equation:

$$P(\lambda) = \frac{S(\lambda) - S_b(\lambda)}{S_p(\lambda) - S_b(\lambda)} P_s(\lambda) \quad \text{(Equation 1)}$$

where $\lambda$ is wavelength in nanometers, $P(\lambda)$ is the fluorescence spectrum of the sample 11 under the ultraviolet radiation source at the wavelength selected in step 23; $S(\lambda)$ is the measured digital count of the sample 11; $S_p(\lambda)$ is the digital count of the standard spectral radiance source; $S_b(\lambda)$ is the digital account of the black calibration, fluorescence spectrum is outputted as a spectrum file of fluorescence spectral radiation by the computer 13.

The ultraviolet fluorescence spectrum $P(\lambda)$ obtained from Equation 1 is used for calculating the colorimetric data in the step of color calculation 25. The calculated colorimetric data include L*, a*, b*, C* and h in the CIELAB color space. L* is lightness, C* is chroma or saturation and h is hue angle. The colorimetric data is outputted as a data file by the computer 13.

According to another aspect of the invention, the measurement parameter time for controlling the fluorescence spectral measurement obtained in step 22 can be adjusted manually or automatically. By increasing the measurement time, the ultraviolet fluorescence spectrum can be amplified by 10, 100, 1000 et al times. The fluorescence peaks of the amplified ultraviolet fluorescence spectrum are enhanced in details for diamond and gemstone identification, spectroscopy study and other purposes.

Other embodiments of the invention will appear to those skilled in the art from consideration of the specification and practice of the invention disclosed herein. It is intended that the specification and the description set forth herein is to be considered as exemplary only, within a true scope and spirit of the invention being indicated by the following claims.

Insofar as the description above and the accompanying drawing disclose any additional subject matter that is not within the scope of the single claim below, the inventions are not dedicated to the public and the right to the one or more applications to claim such additional inventions is reserved.

What is claimed is:

1. A fluorescence spectral measurement and fluorescence color measurement apparatus comprising:
   a spectrometer for measuring the fluorescence spectrum of a sample:
   a dual integrating sphere measurement arrangement that is configured to house a sample, provide ultraviolet radiation on the sample, collect fluorescent light from the sample, and transmit the fluorescent light to the spectrometer;
   the spectrometer is configured to separate the fluorescent light into a spectrum, convert the spectrum into digital signals, and send the digital signals to a computer;
   the computer is configured to calculate measurement parameters of the sample, control the spectrometer, calculate the fluorescence spectrum of the sample and calculate the fluorescence color of the sample;
   said dual integrating sphere measurement arrangement includes:
   a sample integrating sphere that is configured to provide a diffuse white measuring environment for the sample, which sample integrating sphere has a bottom, an internal area, an ultraviolet emission source, and an open area;
   a measurement integrating sphere with at least one lens system port, a light port, an internal area, an open area, and a top;
   a sample platform connecting the measurement integrating sphere to the sample integrating sphere, the sample platform having an upper surface, a bottom surface, and a middle, the sample platform contains a round hole called a measurement aperture;
   a measurement aperture set on the sample platform, the measurement aperture filter is configured to accommodate the sample; a lens system attached to the measurement integrating sphere and configured to receive fluorescent light from the sample;

an ultraviolet emission source that is retained on the top of the sample integrating sphere to provide ultraviolet radiation;

said ultraviolet emission source is installed on the top of the sample integrating sphere to provide ultraviolet radiation on the sample;

the ultraviolet emission source is selected from at least one of an ultraviolet lamp, an ultraviolet fluorescence lamp, an arc lamp, a filtered arc lamp, an ultraviolet laser, and a light emitting diode (LED); and said ultraviolet emission source is connected to a group of electronic circuits selected from at least one of a current limiting resistor in series, a voltage converter, a voltage regulator, a current regulator, and a voltage divider.

2. A fluorescence spectral measurement and fluorescence color measurement apparatus in accordance with claim 1 further comprising: the bottom of said sample integrating sphere is located on the upper surface of the sample platform on the top of the measurement integrating sphere.

3. A fluorescence spectral measurement and fluorescence color measurement apparatus in accordance with claim 1 further comprising: the sample integrating sphere can be taken off the apparatus, and the sample integrating sphere can be placed back onto the apparatus.

4. A fluorescence spectral measurement and fluorescence color measurement apparatus in accordance with claim 1 further comprising: the open area of said sample integrating sphere is equal to or larger than said measurement aperture filter and exceeds 1 percent of the internal area of the sample integrating sphere.

5. A fluorescence spectral measurement and fluorescence color measurement apparatus in accordance with claim 1 further comprising: the total area of the measurement aperture, light trap, lens system port and light port of said measurement integrating sphere does not exceed 50 percent of the internal area of the measurement integrating sphere.

6. A fluorescence spectral measurement and fluorescence color measurement apparatus in accordance with claim 1 further comprising: said measurement aperture filter is set in the middle of said sample platform.

7. A fluorescence spectral measurement and fluorescence color measurement apparatus in accordance with claim 1 further comprising: said measurement aperture filter comprises one or more layers of materials capable of transmit ultraviolet light and visible light in the wavelength range from 200 nm through 800 nm.

8. A fluorescence spectral measurement and fluorescence color measurement apparatus in accordance with claim 1 further comprising: the view field of said leans lens system is restricted to said measurement aperture with a 1 to 25 degree viewing angle from normal to said measurement aperture.

9. A fluorescence spectral measurement and fluorescence color measurement apparatus in accordance with claim 1 further comprising: said sample integrating sphere is configured to accommodate the sample in the middle of said measurement aperture filter in a table-down position.

10. A fluorescence spectral measurement and fluorescence color measurement apparatus in accordance with claim 1 further comprising: in place of the spectrometer, there is a replacement selected from the group consisting of a spectrophotometer, a spectral imaging system, a spectral graphic system and a spectroradiometer.

11. A fluorescence spectral measurement and fluorescence color measurement apparatus in accordance with claim 1 further comprising: said ultraviolet emission source emits ultraviolet radiation in the wavelength range from 200 nm to 400 nm.

12. A fluorescence spectral measurement and fluorescence color measurement apparatus in accordance with claim 1 further comprising: said ultraviolet emission source emits a short wavelength ultraviolet radiation at 254 nm of mercury emission line for a short wavelength ultraviolet fluorescence measurement.

13. A fluorescence spectral measurement and fluorescence color measurement apparatus in accordance with claim 1 further comprising: said ultraviolet emission source emits a long wavelength ultraviolet radiation at 365 nm of mercury emission line for a long wavelength ultraviolet fluorescence measurement.

14. A fluorescence spectral measurement and fluorescence color measurement apparatus in accordance with claim 1 further comprising: said ultraviolet emission source is powered by a group of electric power supplies including at least one of a switch power supply, a regular power supply, and specially designed power supplies.

15. A fluorescence spectral measurement and fluorescence color measurement apparatus in accordance with claim 1 further comprising: said ultraviolet emission source is powered by a 5 volt direct current power supply provided by a computer and electronic devices having a USB port.

16. A fluorescence spectral measurement and fluorescence color measurement apparatus in accordance with claim 1 further comprising: said group of electronic circuits are powered by a group of electric power supplies selected from at least one of a switch power supply, a regular power supply, and a specially designed power supply.

17. A fluorescence spectral measurement and fluorescence color measurement apparatus in accordance with claim 16 further comprising: said group of electronic circuits are powered by a 5 volt direct current power supply provided by the USB of a computer and electronic devices having a USB port.

* * * * *